(12) United States Patent
Ikeda (10) Patent No.: US 7,879,058 B2
(45) Date of Patent: Feb. 1, 2011

(54) LANCET DEVICE FOR FORMING INCISION

(75) Inventor: Yoshiaki Ikeda, Okayama (JP)

(73) Assignee: Asahi Polyslider Company, Limted, Osaka (JP)

( * ) Notice: Subject to any disclaimer, the term of this patent is extended or adjusted under 35 U.S.C. 154(b) by 622 days.

(21) Appl. No.: 11/587,539

(22) PCT Filed: Apr. 22, 2005

(86) PCT No.: PCT/JP2005/007698

§ 371 (c)(1),
(2), (4) Date: Feb. 15, 2007

(87) PCT Pub. No.: WO2005/102166

PCT Pub. Date: Nov. 3, 2005

(65) Prior Publication Data
US 2007/0225741 A1      Sep. 27, 2007

(30) Foreign Application Priority Data
Apr. 26, 2004   (JP) .............................. 2004-129722

(51) Int. Cl.
*A61B 17/14*   (2006.01)
*A61B 17/32*   (2006.01)
*A61B 5/00*    (2006.01)

(52) U.S. Cl. ........................ 606/182; 606/181; 600/583

(58) Field of Classification Search ......... 606/167–185; 600/583
See application file for complete search history.

(56) References Cited

U.S. PATENT DOCUMENTS

| 4,230,118 | A | * | 10/1980 | Holman et al. ............... 606/182 |
| 4,628,929 | A | | 12/1986 | Intengan et al. |
| 4,643,189 | A | | 2/1987 | Mintz |
| 5,133,730 | A | * | 7/1992 | Biro et al. .................... 606/182 |
| 5,314,441 | A | | 5/1994 | Cusack et al. |
| 5,545,174 | A | | 8/1996 | Schenk et al. |
| 5,630,828 | A | | 5/1997 | Mawhirt et al. |
| 5,755,733 | A | * | 5/1998 | Morita ........................ 606/182 |
| 5,782,852 | A | | 7/1998 | Foggia et al. |
| 5,851,215 | A | | 12/1998 | Mawhirt et al. |
| 6,042,595 | A | * | 3/2000 | Morita ........................ 606/181 |
| 2005/0143771 | A1 | * | 6/2005 | Stout et al. .................. 606/181 |

FOREIGN PATENT DOCUMENTS

JP     2000-245715     9/2000

OTHER PUBLICATIONS

Supplementary European Search Report issued Mar. 24, 2009 in counterpart European Application No. EP 05734061.4.

* cited by examiner

*Primary Examiner*—Anhtuan T Nguyen
*Assistant Examiner*—Jocelin C Tanner
(74) *Attorney, Agent, or Firm*—Wenderoth, Lind & Ponack, L.L.P.

(57) ABSTRACT

An incision device capable of preventing inadvertent firing, and including a covered attached to the device. The incision device comprises a housing, and a lancet guide assembly having lancet guides and a lancet body. The lancet body further comprises a lancet blade. The lancet blade is covered by a removable protective cover having a stopper which prevents a trigger arm from being moved so as to fire the lancet blade.

23 Claims, 11 Drawing Sheets

LANCET DEVICE FOR FORMING INCISION

TECHNICAL FIELD

This invention generally relates to a lancet device for forming an incision, preferably a precisely controlled incision in the skin or other bodily surface of a patient, for example in a heel (which is also referred to as an incision device hereinafter), and, more particularly, to a disposable incision device which can be manufactured economically, has a very stable construction and makes it possible to suppress improper use by a user.

BACKGROUND ART

Various different types of devices are commercially available which can be used to puncture or pierce a patient's skin. These include devices, such as those disclosed in U.S. Pat. Nos. 5,133,730 and 5,755,733, which are designed to prick the patient skin, for example a finger tip, as well as devices that are configured to form an incision of a uniform length and depth in the skin.

As will be appreciated, devices which can produce a precisely controlled uniform incision can be used in conjunction with a variety of different medical tests, procedures and so on including, for example, bleed time tests and drawing blood for subsequent collection. More particularly, one important use for such incision devices is to form an incision in the skin of an infant, generally in the heel, so as to enable blood to be collected for tests, such as metabolic screening tests.

Available incision devices generally utilize a spring arrangement to produce the energy necessary to drive the cutting blade through the patient's skin. With these devices, such as the device disclosed in U.S. Pat. No. 4,643,189a spring is typically assembled into the device in a biased condition so that it is storing the energy which will be used to drive the cutting blade when the device is triggered. The biased spring, however, adversely affects the stability of the device. In particular, the biased spring can make accidental or premature triggering or discharge of the device, which can occur simply through inadvertent touching of the trigger, much more likely. Moreover, having the spring in the biased condition also places many of the other components of the device under stress resulting in an overall reduction in the shelf-life of the device.

Since it is generally preferable to design these devices so that they are disposable after a single use, manufacturing and assembly costs are always important considerations for producing a commercially viable product. However, assembling the spring in the biased condition makes the device more difficult to manufacture, sometimes requiring the provision of special jigs, and resulting in increased manufacturing and assembly costs for the device. Additionally, if provisions, such as safety caps, are included to help prevent premature firing or discharge of the device, it can further increase materials, and manufacturing and assembly costs for such provisions.

In order to solve the above problems, Japanese Patent Kokai Publication No. 2000-245715 provides an incision device which is intended to achieve the following: being manufactured and assembled in a cost-effective manner, forming a uniform incision through in the skin, having a stable construction which helps prevent inadvertent discharge of an incising element and enables the device to have a long shelf-life, and being packaged while being sterilized in a cost-effective manner. With such device, most of the above problems are substantially solved, so that it can generally be said to be a satisfactory incision device.

Patent Reference 1: U.S. Pat. No. 5,133,730
Patent Reference 2: U.S. Pat. No. 5,755,733
Patent Reference 3: U.S. Pat. No. 4,643,189
Patent Reference 4: Japanese Patent Kokai Publication No. 2000-245715

DISCLOSURE OF THE INVENTION

Problems to Be Solved by the Invention

In view of the foregoing, known disposable skin incision devices can be said to be almost satisfactory. However, it is desirable to solve problem(s) when such devices are actually produced and supplied. Therefore, the present invention intends to identify the presence of such a problem(s) and then to solve the same.

Means to Solve the Problems

The present inventor carried out intensive studies as to the above mentioned further problem(s), and the following problem has been found as to the incision device disclosed in Japanese Patent Kokai Publication No. 2000-245715: when a user of the device inadvertently depresses a trigger arm into a housing toward a firing position while holding the device with fingers, the trigger arm pivots even though a protective cover is attached to a lancet blade, so that the blade is fired with the protective cover, that is, the blade together with the cover pivots, which makes it impossible to use the incision device (thus, such device becomes wasted). That is, the inventor has found that there is a problem with regard to the device disclosed in Japanese Patent Kokai Publication No. 2000-245715 and such problem is to be solved, and then reached the present invention which will be explained below.

The present invention provides a novel incision device with which inadvertent discharge together with the cover attached is prevented as much as possible. Such incision device comprises a housing and a lancet guide assembly having a lancet body and a lancet guide wherein the lancet body comprises a blade which is covered with a removable protective cover having a stopper which prevents an trigger arm from moving so as to fire the lancet blade. The stopper is located on a certain position of a locus which is formed by the trigger arm when the trigger arm moves so as to fire the lancet blade, so that the movement of the trigger arm is prevented. It is noted that the incision device according to the present invention may be substantially the same as the incision device disclosed in Japanese Patent Kokai Publication No. 2000-245715 (or its corresponding U.S. Pat. No. 6,045,295) except that the incision device includes the trigger arm which has the above mentioned stopper. Thus, the contents of the patent publication(s) are incorporated herein by the reference thereto.

In the incision device according to the present invention, the lancet guide assembly includes a lancet body mounted within the housing for pivotal movement and a lancet guide. The guide guides the lancet blade through an arcuate cutting stroke during which the lancet blade extends through an opening in the housing as the lancet body is pivoted between an unfired position and a fired position (i.e. a position after firing). Such lancet guide is composed of a guide member provided on the lancet body and a complementary guide member provided on the housing, and those members cooperate to ensure that the lancet blade passes through a predetermined path. Concretely, the guide member is a convex portion which the lancet body includes as described below, and the complementary guide member comprises a guide recess located in the housing which guides the convex portion. In other embodiment, the guide member is a concave portion, and the complementary guide member comprises a guide protrusion located in the housing which guides the concave portion.

The incision device according to the present invention also includes a trigger mechanism having a trigger arm mounted in the housing for pivotal movement between a ready-to-fire position and a firing position. A spring element is arranged within the housing such that it is an unbiased condition when the trigger arm is in the ready-to-fire position and is biased as the trigger arm pivots towards the firing position. The trigger mechanism and the spring element are configured such that the biased spring element is released when the trigger arm reaches the firing position, and the spring is arranged such that when it is released, it exerts a force on the lancet body which pivots the lancet body from the unfired position to the fired position and thereby moves the lancet blade through the cutting stroke.

Effects of the Invention

In the incision device according to the present invention, the protective cover includes the stopper, so that the movement of the trigger arm is prevented unless the protective cover is removed. Thus, when the protective cover is in an attached condition to the device, the trigger arm cannot fire the lancet even though the trigger arm is pressed into the housing.

DETAILED DESCRIPTION OF THE INVENTION

Those and other features and advantages of the invention will be more readily apparent upon reading the following description of preferred exemplary embodiments of the invention and upon reference to the accompanying drawings. While the invention will be described and disclosed in connection with certain preferred embodiments and procedures, it is not intended to limit the invention to those specific embodiments or procedures. Rather it is intended to cover all such alternative embodiments and modifications as fall within the spirit and scope of the invention.

Figure 1:
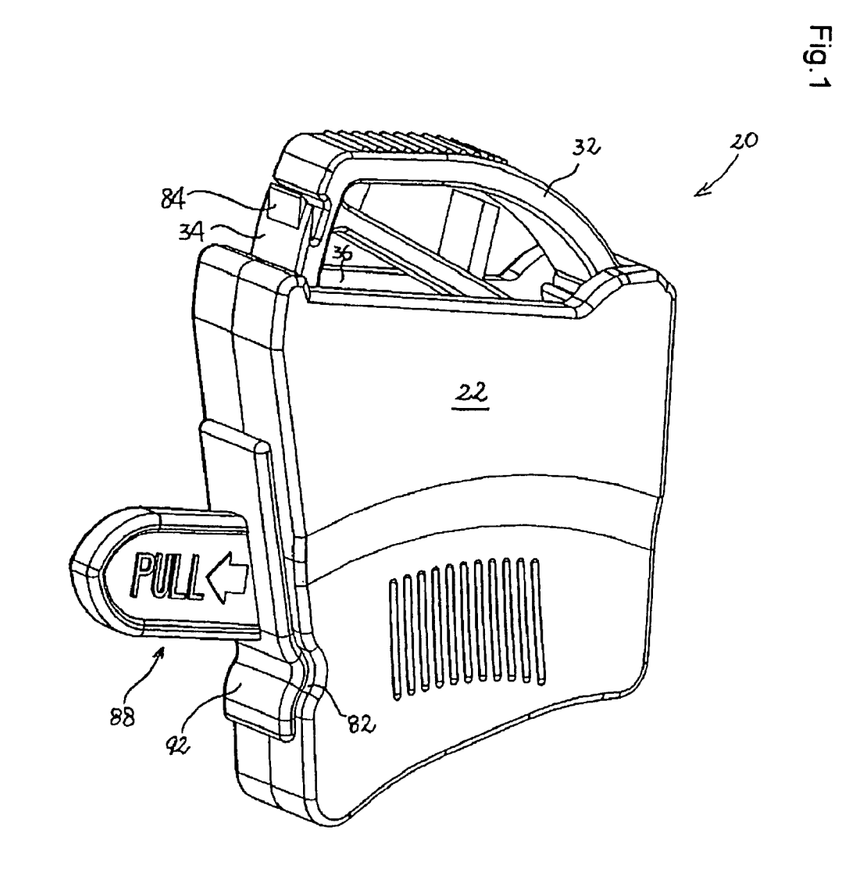
FIG. 1 is a schematic perspective view of an illustrative skin incision device constructed in accordance with the teachings of the present invention.
Figure 2:
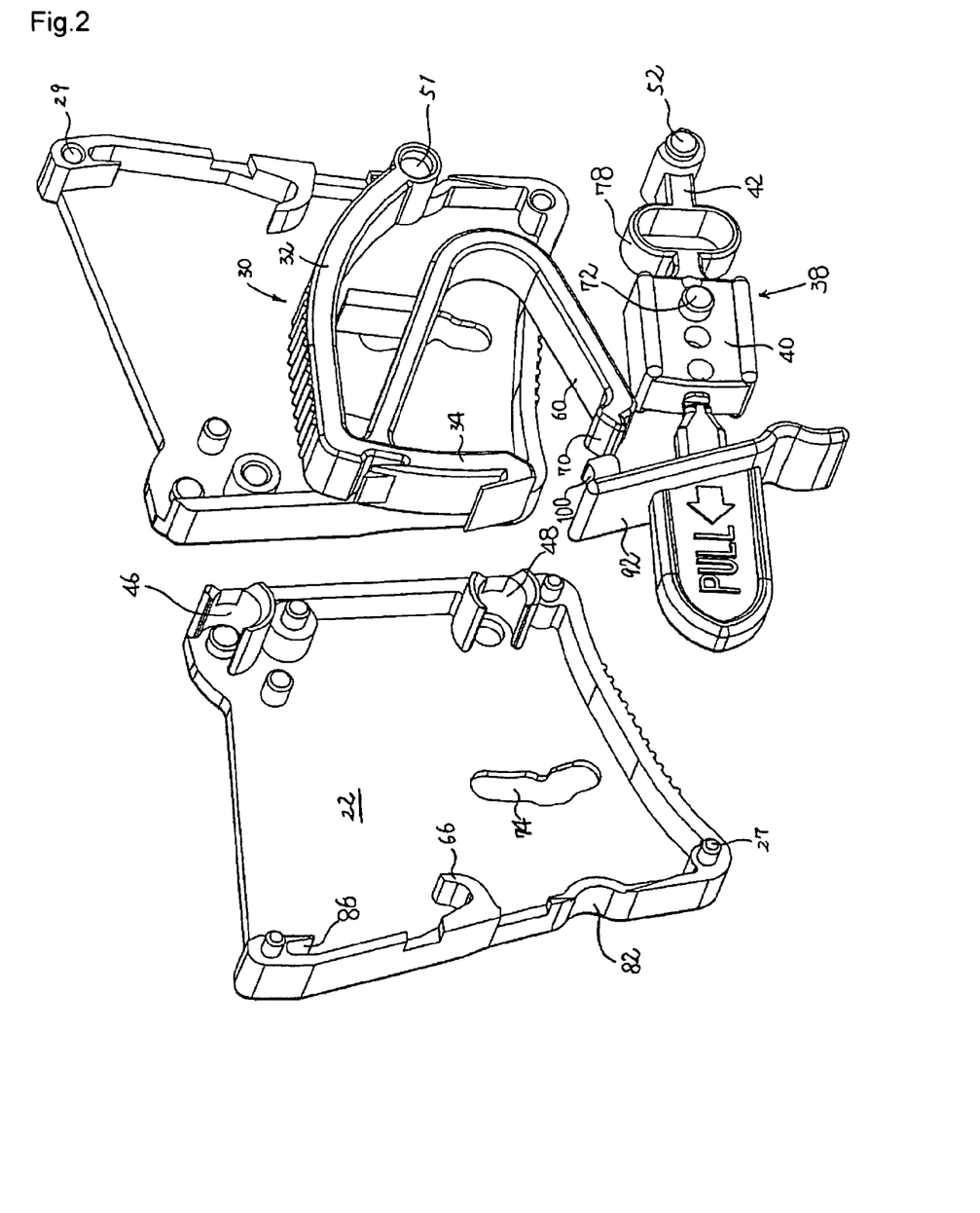
FIG. 2 is a schematic exploded perspective view of the incision device.

Referring now more particularly to FIGS. 1 and 2, there is shown an illustrative incision device 20 which can be used to produce an incision of a precisely controlled length and depth in a bodily surface of a patient, for example a heel, in accordance with the present invention. The incision device of the present invention has a relatively simple and very stable construction, makes it difficult to trigger the device inadvertently, and also enables itself to have a relatively long shelf-life even at elevated temperatures.

Figure 3:
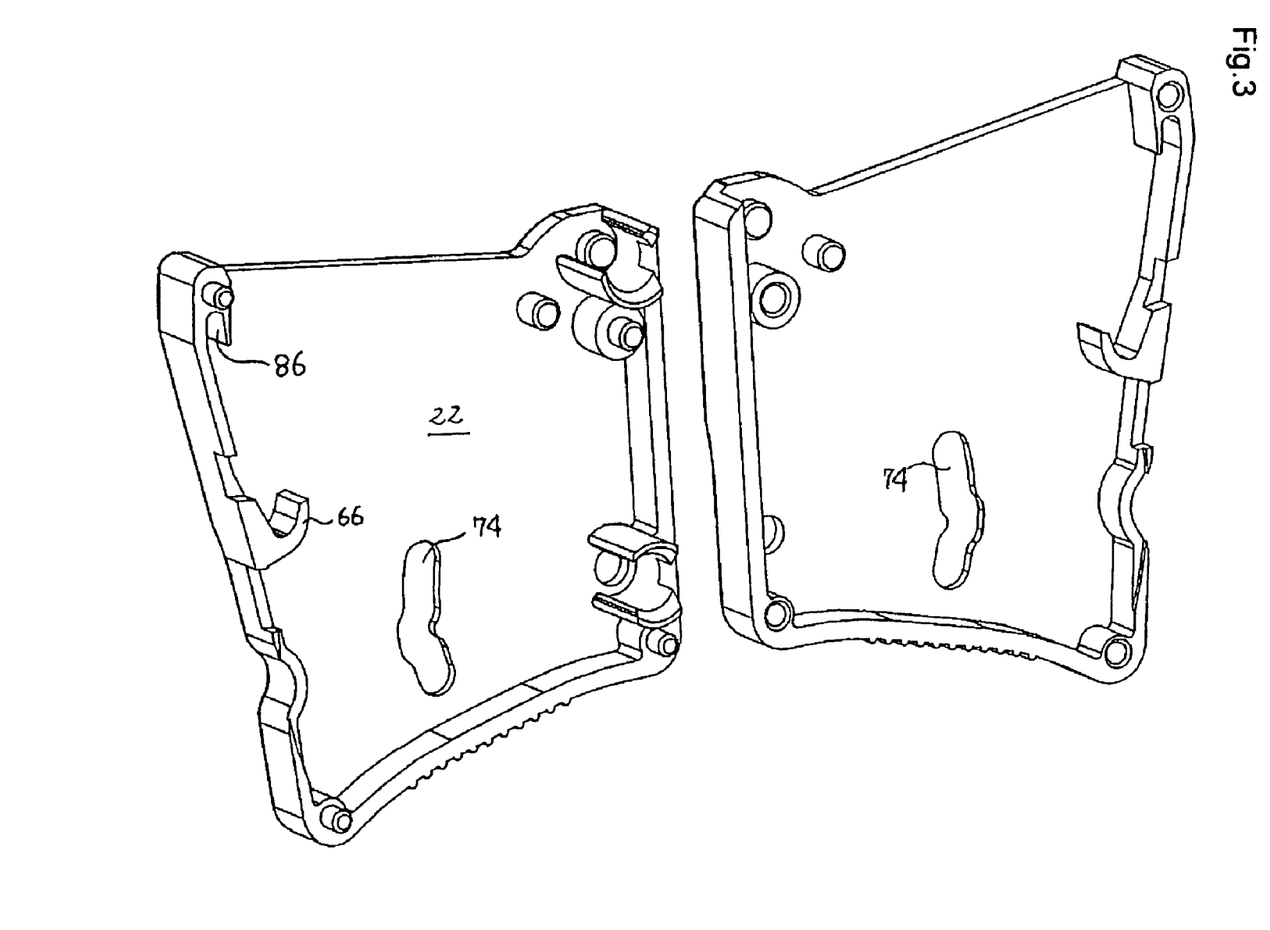
FIG. 3 is a schematic perspective view of the housing of the incision device.
Figure 4:
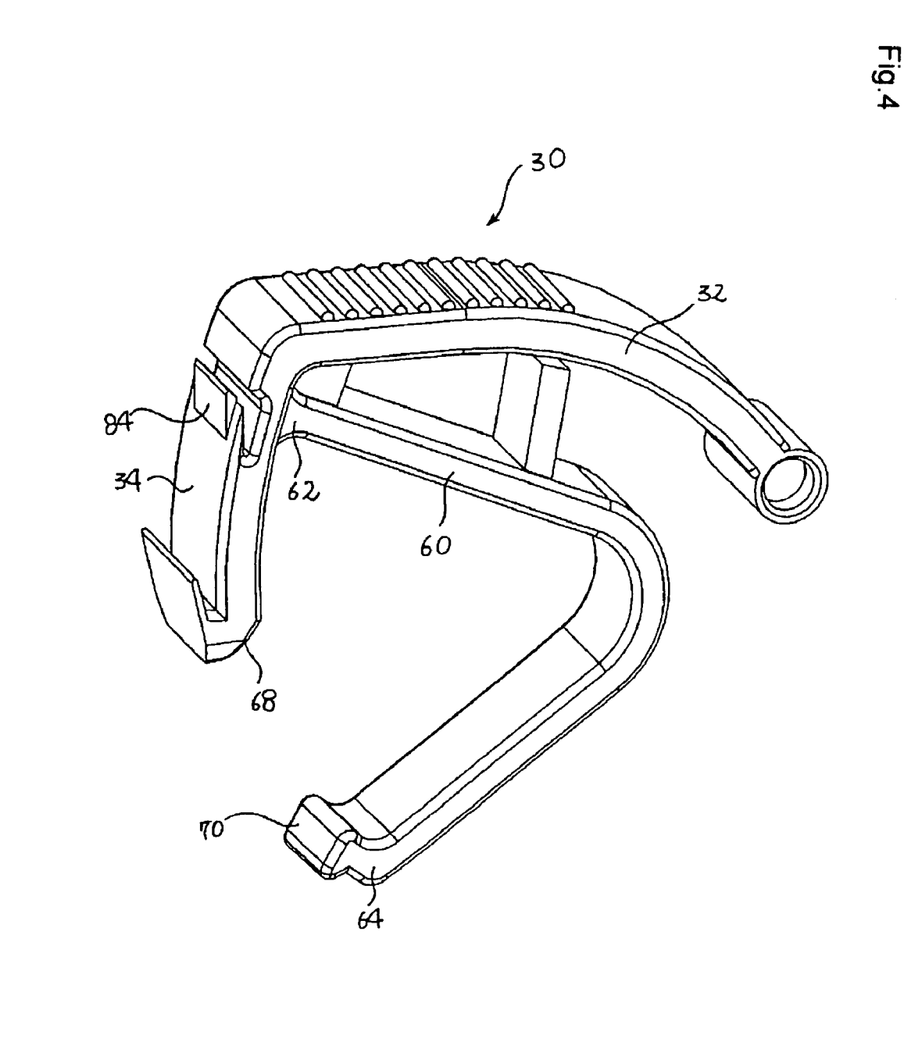
FIG. 4 is a schematic perspective view of the trigger mechanism of the incision device which mechanism comprises the spring element of the incision device.

The illustrated incision device 20 generally includes a housing 22, a lancet body 38 comprising an incising element or lancet blade 24, which in this instance incorporates an inclined cutting edge (see FIG. 7), and a trigger mechanism 30. The lancet body 38 and the trigger mechanism 30 upon triggering moves the lancet blade through a cutting stroke that can create a precise incision in the skin of a patient. As shown in FIG. 3, the housing 22, in this instance, comprises two identical mating halves which can be formed of a plastic resin material. In the illustrated embodiment, the two halves of the housing 22 have a mating post (or convex portion) 27 and recess (or concave portion) 29 arrangement at the corners of the opposing side such that the two halves of the housing can be snapped together. In other embodiment, those two halves may be connected together at one side thereof by a hinge 28.

Figure 8:
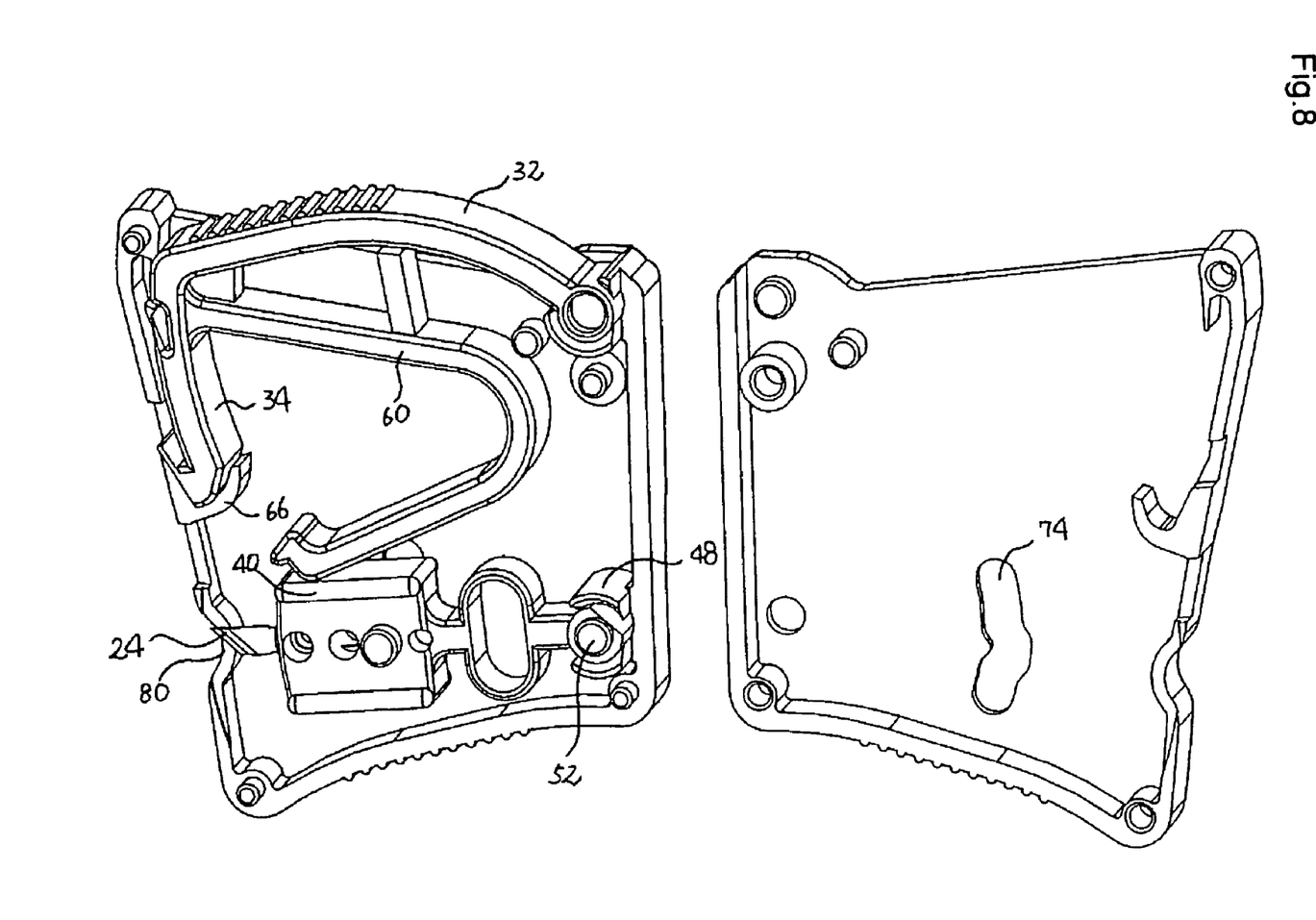
FIG. 8 is a schematic perspective view of the incision device similar to that shown in FIG. 6 wherein the trigger arm has fully been depressed into the firing position and the spring element is discharging the lancet blade so as to drive the lancet blade through its cutting stroke.

For actuating or firing the incision device 20, the device 20 includes a trigger means or mechanism 30 movable between a ready-to-fire position (e.g., shown in FIGS. 1 and 6) and a firing position (e.g., shown in FIG. 8). The trigger mechanism 30, in this case, includes a trigger arm 32 having a trigger actuating element 34. As shown in FIG. 1, the trigger arm 32 extends angularly through an opening 36 in the top of the housing 22 and away from the housing so as to be easily accessible for actuation by a user. The trigger actuating element 34 is connected to the trigger arm 32 adjacent the free end thereof (the left with reference to FIG. 1) and extends away from the trigger arm 32 and back towards and into the housing through the opening 36. As is described in greater detail below, the trigger mechanism 30 can be used to actuate the incision device through depressing the trigger arm 32 such that it is displaced downwardly towards the housing.

The lancet body 38 supports and guides the lancet blade 24 when the blade 24 moves through its cutting stroke as described above. In the illustrated embodiment, the lancet body 38 includes a lancet blade holder 40 which is connected to a lever or guide arm 42, and the lancet body 38 is movable between an unfired position (see, e.g., FIGS. 6 and 7) and a fired position (see, e.g., FIG. 11). In the illustrated embodiment, lancet holder blade holder 40 is integrated with the lancet arm 42, but they may be separate members which are assembled together.

In order to allow the trigger arm 32 and the lancet body 42 to pivot, pivot axes 51 and 52 are provided to their pivoting ends, and bearing portions 46 and 48 which bear the axes are also provided. In the illustrated embodiment, the trigger mechanism 30 and the lancet body 38 are separate members respectively. They may be, however, integrated with an intermediate member which connects them together so as to form a single piece structure. In this case, notches may be provided between them and the intermediate member so as to allow pivoting around the notches.

For driving the lancet body 38, and in turn, the lancet blade 24, through the cutting stroke, the incision device according to the present invention includes a spring means or element 60. In accordance with one aspect of the present invention, in order to provide the incision device 20 with a more stable construction, the spring element 60 can be configured such that it can be assembled into the device in an unbiased condition and remain in that unbiased condition until the device is actuated or fired. Accordingly, the incision device 20 is easier to assemble. Moreover, since the spring element 60 is not biased, it does not apply any force which would stress other elements (for example, the lancet arm 32) of the incision device, thus, malfunctions are much less likely even when the device has been stored for a relatively long period of time or at elevated temperature. Additionally, in the illustrated embodiment, the spring element 60 is integrated directly into the trigger mechanism 30.

Figure 6:
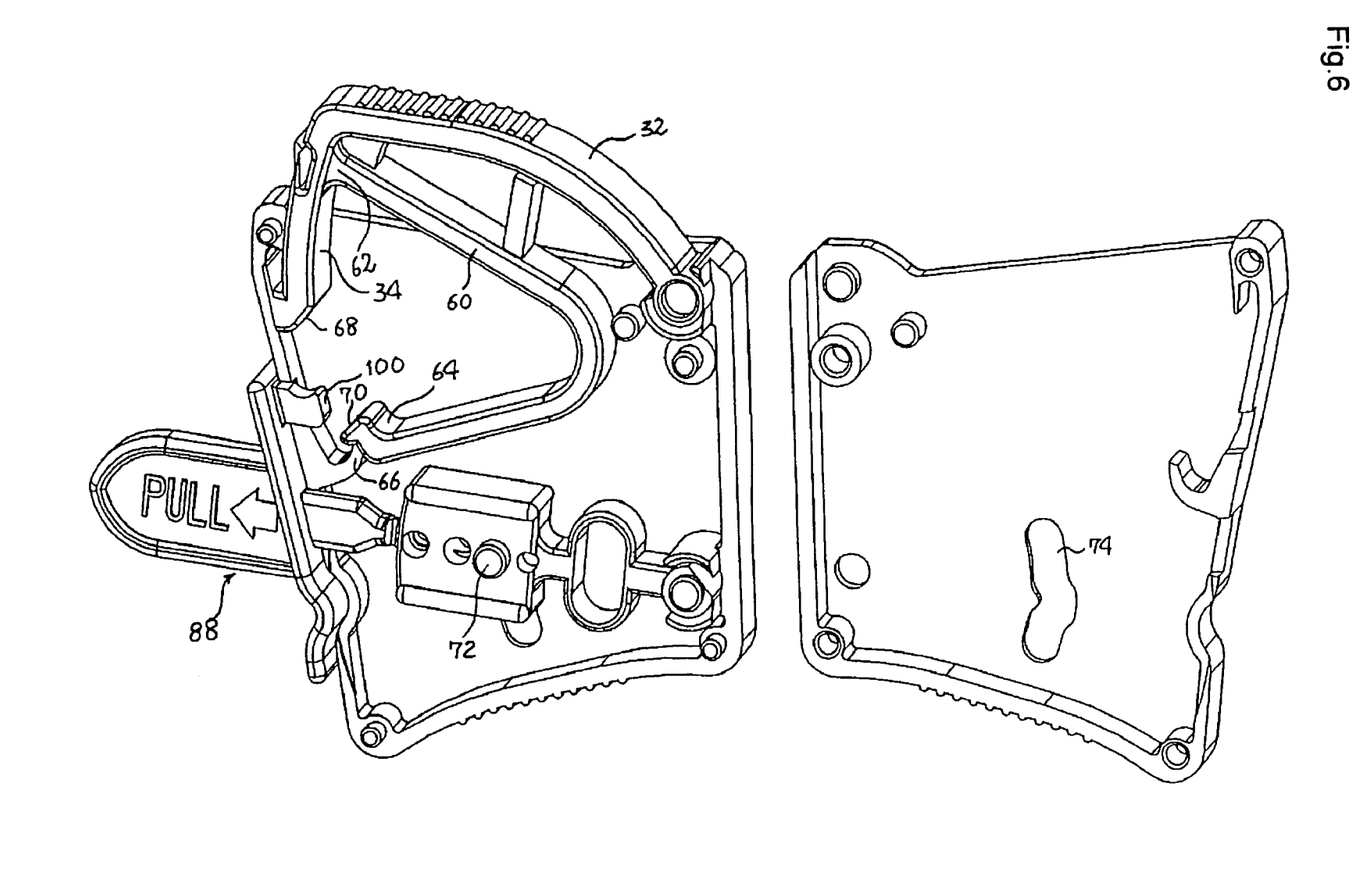
FIG. 6 is a schematic perspective view of the incision device while the housing is opened in a ready-to-fire condition prior to use.
Figure 7:
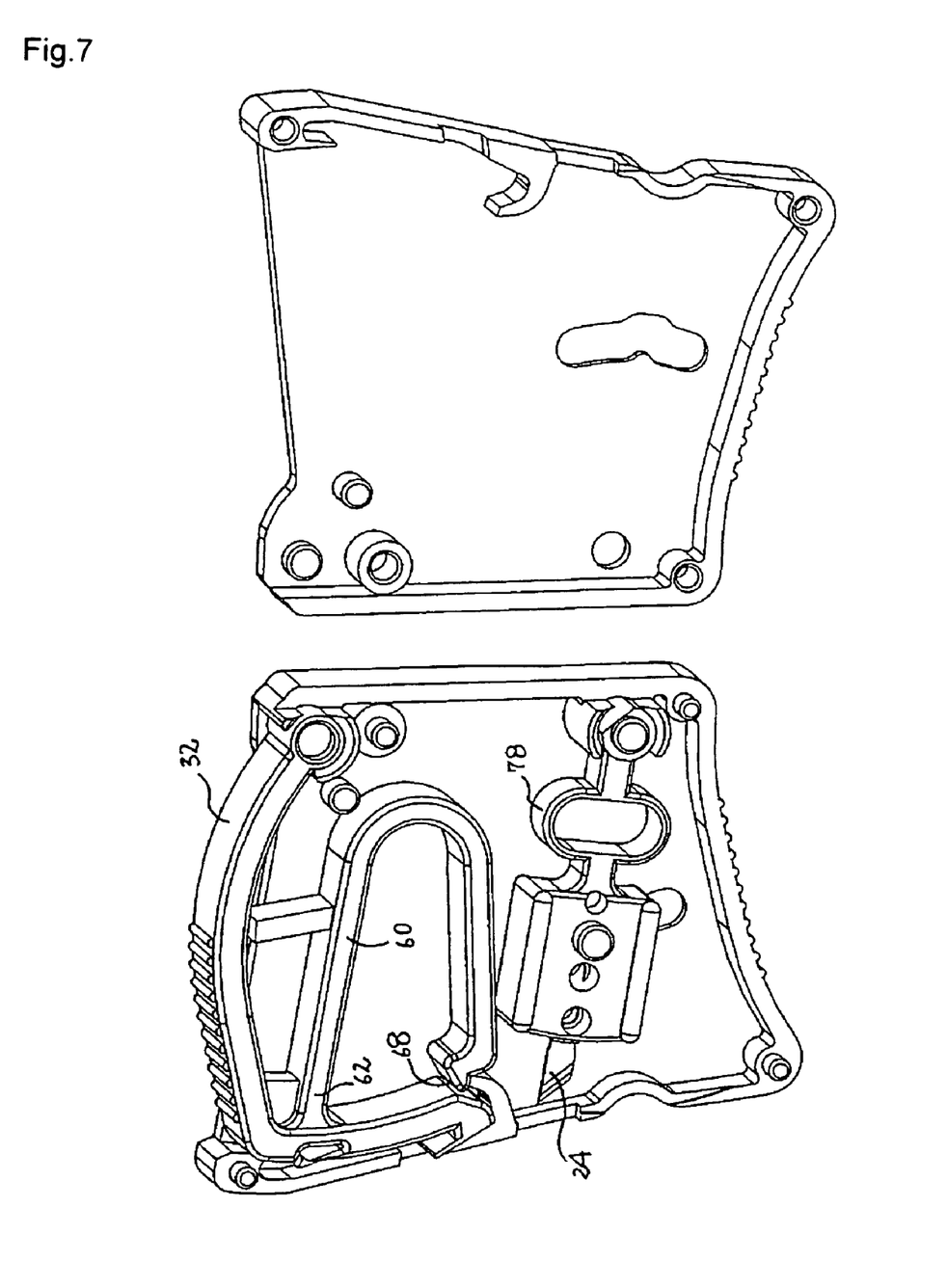
FIG. 7 is a schematic perspective view of the incision device similar to that shown in FIG. 6 wherein the trigger arm almost fully depressed toward the firing position so that the spring element is in a full compression condition.

As shown in FIGS. 6 and 7, the spring element 60 is interrelated with the trigger mechanism 30 such that the movement of the trigger arm 32 from the ready-to-fire position (FIG. 6) towards the firing position biases the spring element 60. In the illustrated embodiment, the spring element 60 has a generally V-shaped configuration and is constructed of a material which enables the spring element to be resiliently compressible. Preferably, the spring element 60 is constructed of a plastic resin material in order to reduce costs, however, it will be appreciated that other materials could be used, including a metal. As shown in FIG. 6, a first end 62 of the spring element 60 is connected to the trigger actuating element 34 while a free end 64 of the spring element is arranged, when the incision device 20 is assembled, in engagement with an internal catch 66 formed on the inside of one side of the housing 22. Thus, when the trigger arm 32 is pivoted towards the firing position such that the state shown in FIG. 6 is converted to the state shown in FIG. 7, the movement of the trigger actuating element 34 causes the first end 62 of the spring element to move towards the free end 64 of the spring element which is held in place by the catch 66, thereby biasing the spring element 60.

As readily seen from the comparison of FIG. 6 with FIG. 7, the lancet body 38 contains the protective cover 88 in FIG. 6 while the cover is removed in FIG. 7. The protective cover 88 covers and protects the lancet blade 24, and also prevents the trigger actuating element 34 from moving toward the catch 66 when the protective cover 88 has not been removed from the blade holder 40. In order to prevent such movement, the protective cover 88 comprises a stopper 100 which is located on a locus formed by the movement of the end of the trigger actuating element 34, (that is, the free end thereof). Therefore, in the state shown in FIG. 6, even though the trigger arm 32 is depressed into, the end of the trigger actuating element 34 abuts against the stopper 100, so that it cannot move ahead any more. However, in the state shown in FIG. 7, the protective cover 88 has been removed. In this situation, it can generally be determined that the user of the device has removed the protective cover 88 for the purpose of using the incision device, and thus the end of the trigger actuating element 34 can move toward the catch 66 as described below. Then, by depressing the trigger arm 32, the free end 64 of the spring member 60 which is held by the catch 66 can be released so as to discharge the lancet blade 24.

For releasing the spring element 60, the trigger actuating element 34 is configured so as to disengage the free end 64 of the spring element from the catch 66 once the spring element 34 is biased and the trigger arm 32 reaches the firing position as shown in FIGS. 7 and 8. More specifically, an inclined cam surface 68 is provided on an end of the trigger actuating element 34 which engages a cooperating cam surface 70 at the end of the spring element 60 to push the free end 64 of the spring element 60 off the internal catch 66 as shown in FIGS. 7 and 8.

Figure 10:
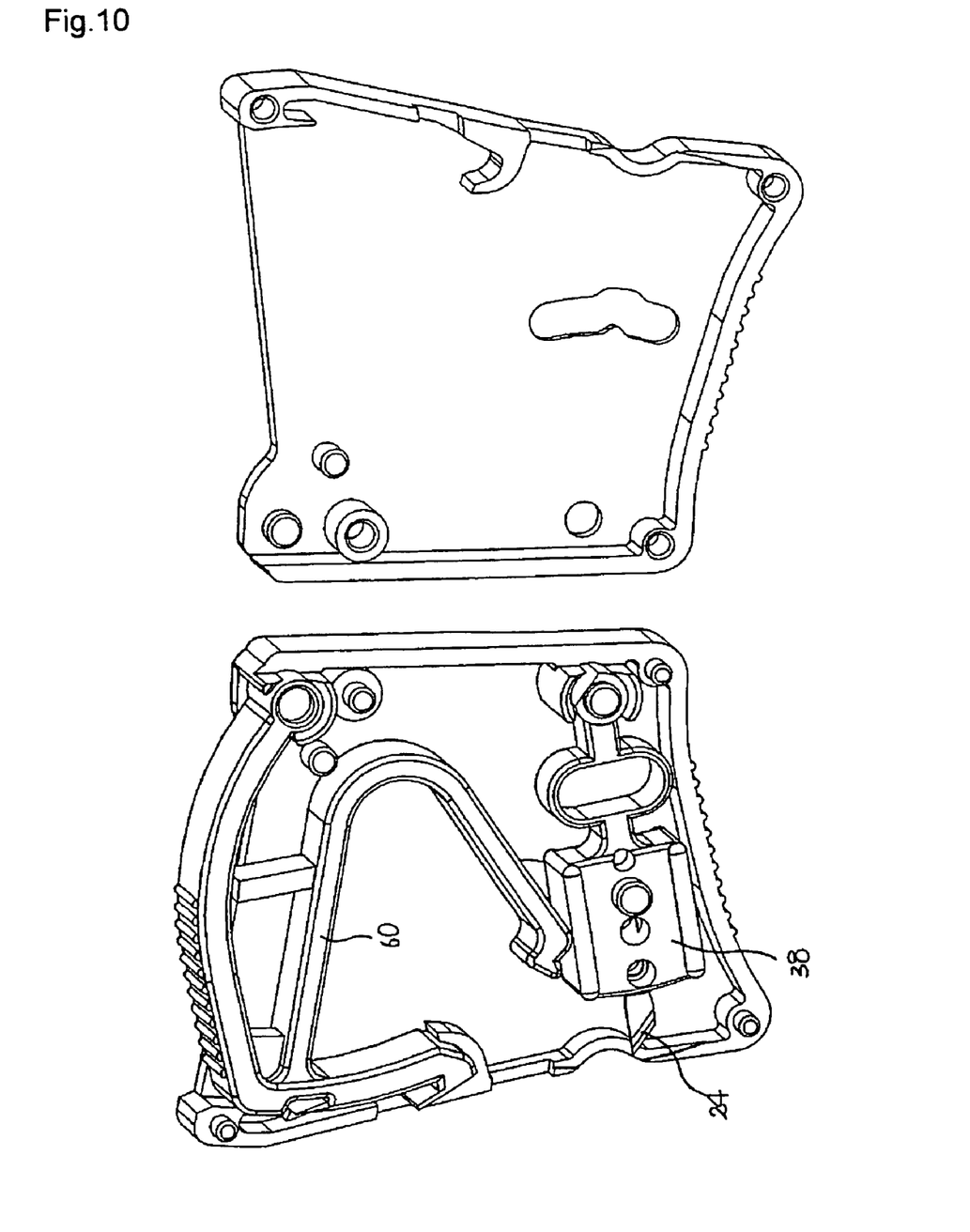
FIG. 10 is a schematic perspective view of the incision device similar to that shown in FIG. 6 wherein the lancet blade is near the end of its cutting stroke.
Figure 11:
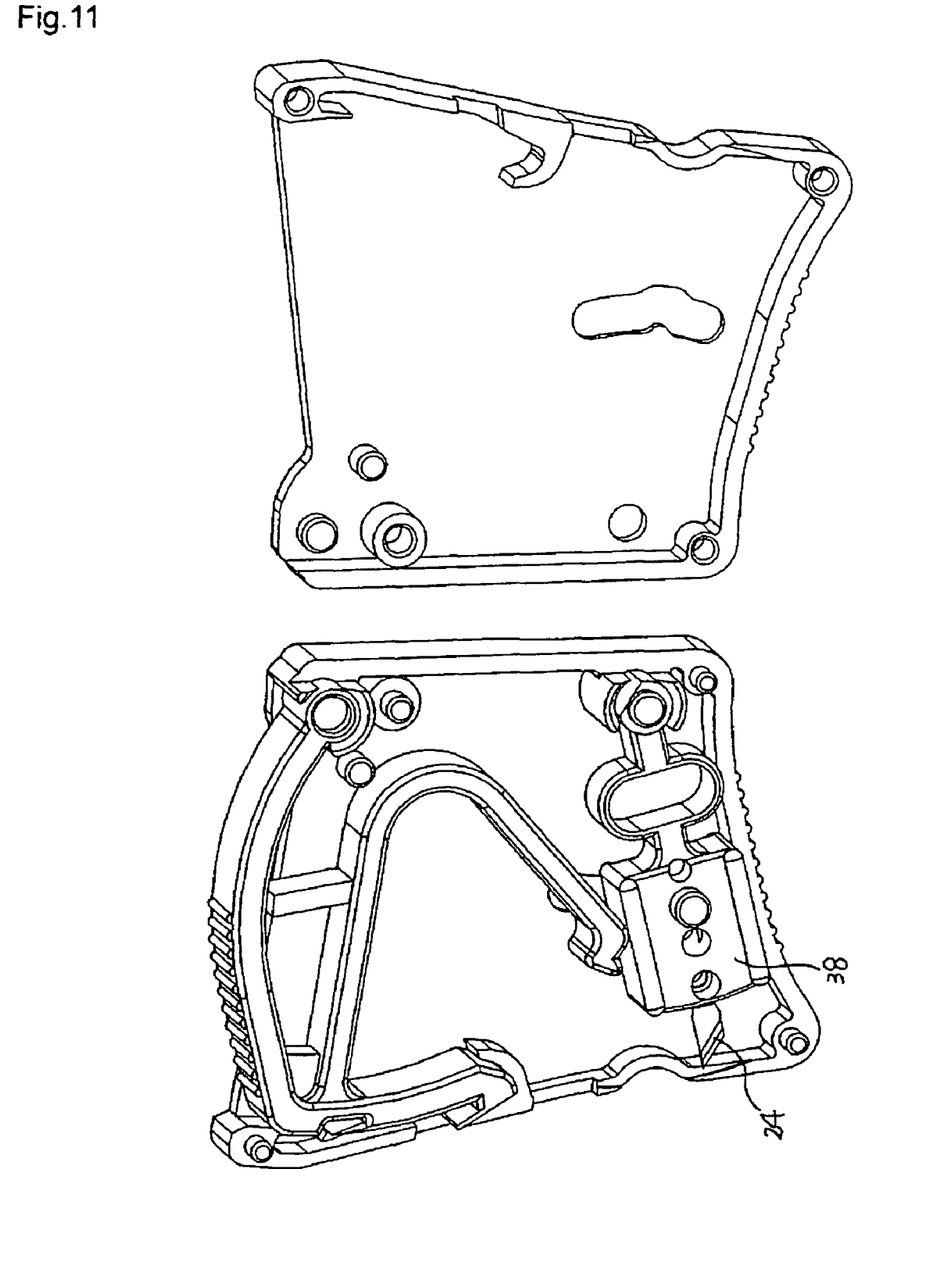
FIG. 11 is a schematic perspective view of the incision device similar to that shown in FIG. 6 wherein a firing sequence has been completed.

In order to drive the lancet blade 24 through the cutting stroke, the spring element 60 is arranged such that when it is released, the free end 64 of the spring element strikes or hammers and then pushes the lancet blade holder 40 of the lancet body 38. As shown in FIG. 8, the initial hammering force causes the lancet body 38 to begin to pivot about the pivot point defined by the pivot axis 52 and the bearing portion 48 of the lancet body, thereby starting movement of the blade holder 40 and, in turn, the lancet blade 24 through an arcuate path. After the initial hammering force is applied, the free end 64 of the spring element 60 comes over the external surface of the blade holder 40 (as shown in FIGS. 8, 10 and 11) and continues to push the blade holder 40 through the arcuate path resulting from the pivotal movement of the lancet body 38 from the unfired position to the fired position.

In order to ensure that the cutting stroke of the lancet blade 24 is precisely controlled, the lancet body 38 is adapted such that the blade holder 40 moves through a precise arcuate path as the lancet body 38 is pivoted between the unfired position and the fired position. Moreover, the lancet arm 42 of the lancet body 38 includes, in this instance, a generally oval-shaped expandable section 78 which permits linear expansion of the guide arm 42, and thus the lancet body 38 as exemplified by the change in shape of the expandable section 78 in FIGS. 7 and 8. As will be appreciated, the expandable section 78 permits a projecting lug 72 of the lancet holder 40 to be guided via an elongated concave portion or groove 74 in the housing through a precise arcuate path, in which the lancet blade 24 is first brought into a cutting position (FIGS. 7-8), then executes a cutting stroke (FIGS. 8-10) and finally moves into a safe at-rest position (FIG. 11).

The expandable section 78 preferably has a shape, such as the oval-shape in the illustrated embodiment, which has bilateral symmetry. The bilaterally symmetrical shape of the expandable section 78 allows the lancet body 38 to expand in a linear direction even though the spring element applies a force in a generally lateral direction, thereby ensuring that precise control over the profile of the arcuate cutting path is maintained. More specifically, the bilaterally symmetrical shape of the expandable section 78 helps prevent the guide arm 42 and thus the lancet body 38 from being angularly deflected as a result of the initial hammering force applied by the spring element 60, the forces resulting from movement of the projecting lugs 72 through the groove 74, and the forces resulting from the lancet blade 24 cutting through the skin.

Figure 9:
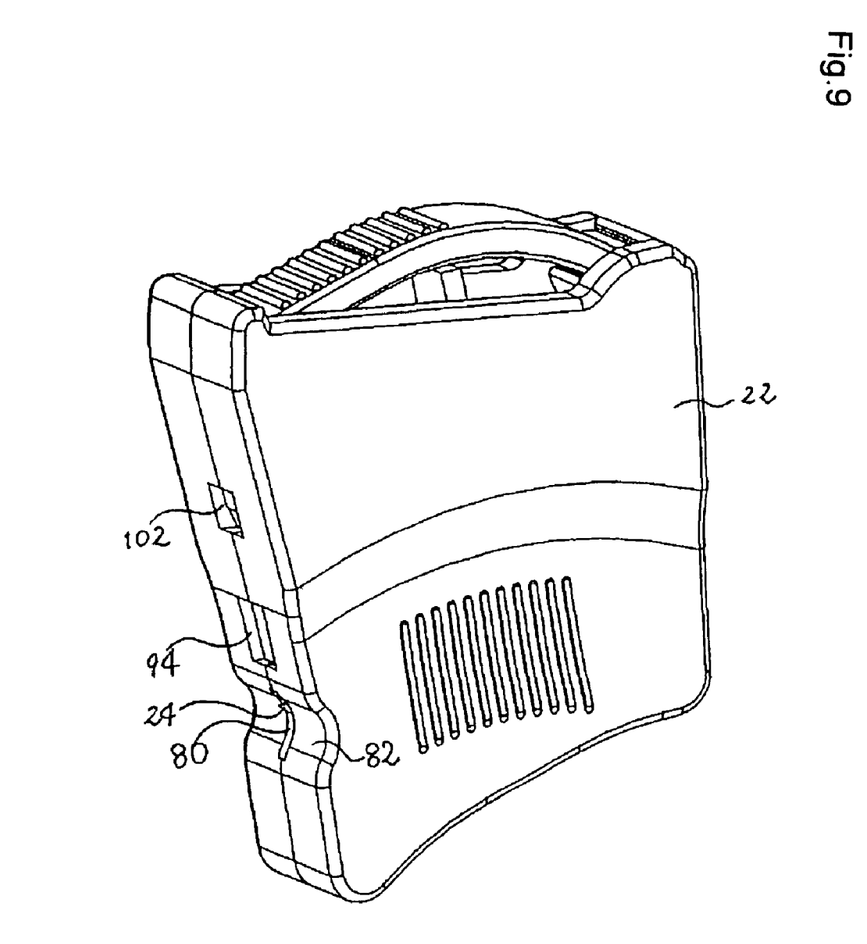
FIG. 9 is a schematic perspective view of the assembled incision device which corresponds to that shown FIG. 8 wherein the lancet blade is moving through its cutting stroke.

As shown in FIG. 7, before the incision device 20 is actuated, the lancet blade 24 is arranged entirely inside of the housing 22. During the firing sequence, the lancet blade 24 first moves into a position wherein the blade extends through a slot 80 formed in an arcuately shaped skin engaging portion 82, as shown, for example, in FIG. 9. The lancet blade 24 then moves through a precise cutting stroke. After the cutting stroke is completed, the configuration of the guiding groove 74 in the housing causes the lancet blade 24 to retract back into the housing, as shown in FIG. 11, so that the incision device can be disposed of without any exposed cutting edges which may cause injury.

Of course, it will be understood that the incision device 20 can be designed to create an incision having a wide variety of different dimensions. For example, in one preferred embodiment, through varying the configuration of the housing 22 (for example, the arcuately shape of the skin engaging portion 82) and/or the shape of the lancet blade 24, an incision device can be provided which is capable of producing an incision of anywhere between approximately 0.5 mm to 2.0 mm in depth.

In order to prevent the incision device 20 from being reused and thereby compromising the sterility of the device, the trigger mechanism 30 is configured such that the device can be fired only once. Specifically, once the trigger arm 32 reaches the firing position, a ridge (or a protrusion) 84 formed on the trigger actuating element 34 engages a cooperating edge 86 formed in the housing 22 to prevent return of the trigger arm 32 toward the ready-to-fire position as shown in FIG. 6. Thus, the engagement of the ridge 84 with the housing prevents the incision device 20 from being re-loaded once it has been fired.

Figure 5:
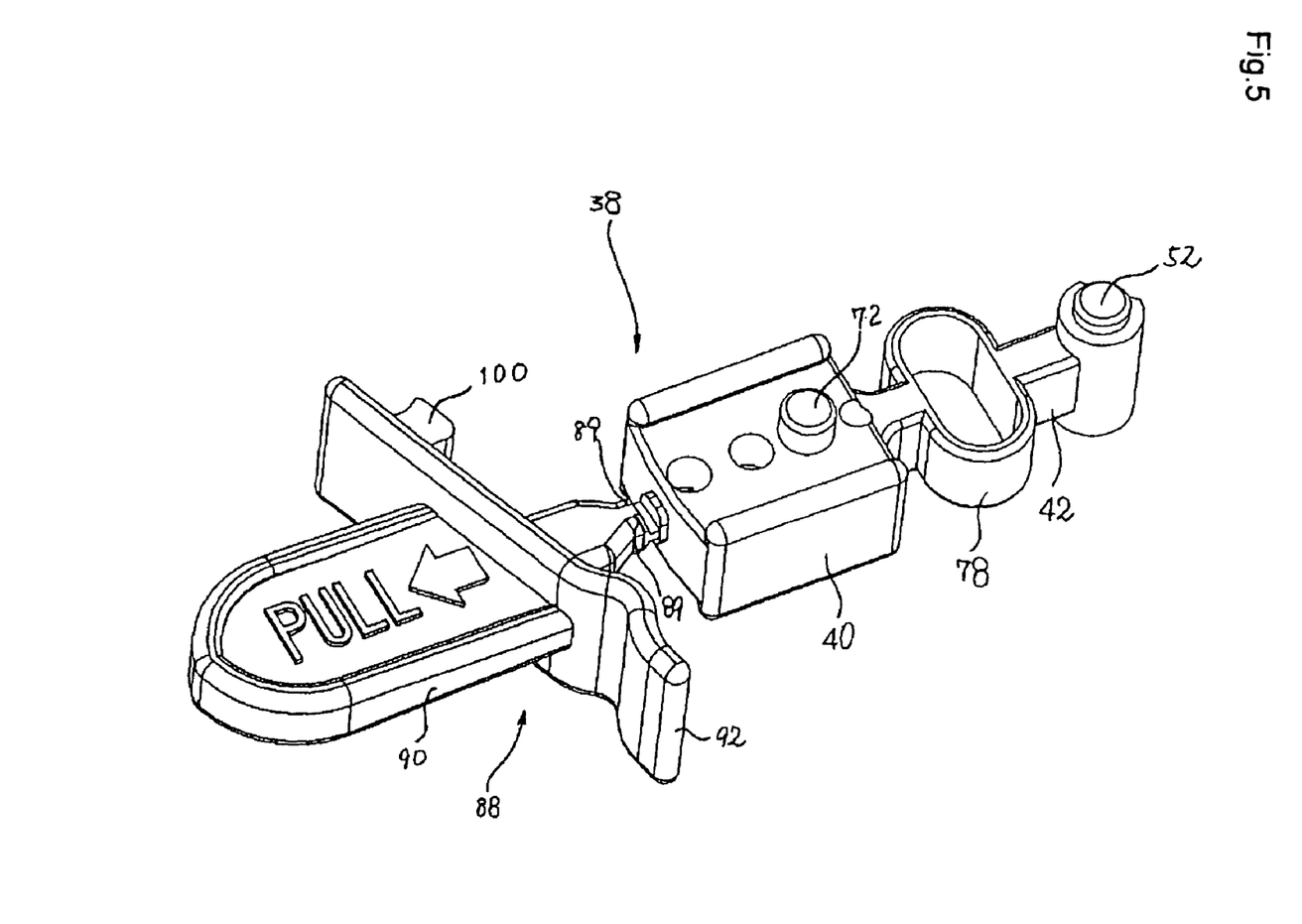
FIG. 5 is a schematic perspective view of the lancet body of the incision device.

To simplify sterilization and packaging of the incision device 20, a removable cover may be provided which covers both the lancet blade 24 and the skin-engaging portion 82 of the housing. More particularly, as shown in FIGS. 1, 5 and 6, the blade holder 40 of the lancet blade 24 is connected to a snap-off or pull-off removable cover 88 which may be disengaged from the blade holder 44 via a pre-cut slit 89 to uncover the lancet blade 24. The slit does not necessarily reach the lancet blade, and the lancet holder and the cover may be connected together through a notch portion.

In the illustrated embodiment, the removable cover 88 includes a protective sheath portion 90 which shields the lancet blade 24 from contamination and a protective flange portion 92 which protects the arcuate skin engaging portion 82 of the housing 30 against contamination. It is noted that in the incision device according to the present invention, the protective flange portion 92 comprises a stopper 100 as described above, which extends into the housing through an opening 102 which is provided to a side of the housing. Such stopper 100 functions to prevent the trigger arm 32 from being depressed inadvertently into the housing until the cover 88 is removed before using the incision device. As shown in FIGS. 1 and 6, the sheath portion 90 of the cover extends through an opening 94 in the side of the housing 22 such that it can be easily grasped and removed from the lancet blade 24, which is arranged entirely within the housing, prior to use of the incision device. When the cover is removed as described, the stopper 100 simultaneously becomes absent, so that the trigger arm is able to forward toward the catch 66. Because of the employment of the removable cover 88 thus described, only the lancet blade 24 itself must be sterilized and thus, there is no need to encase the entire incision device in sterilized packaging.

To use the incision-type device 20, the cover 88 is pulled from the lancet blade 24 through the opening 94 in the housing so as to uncover the cutting edge of the lancet blade 24 and also allow the trigger arm 32 to be depressed while exposing the skin engaging portion 82 of the housing 22. Next, the skin engaging portion 82 of the housing is pressed against a patient's skin. Thereafter, the trigger arm 32 of the trigger mechanism 30 is simply pressed downwardly toward the firing position, as shown, for example, in FIG. 7, in order to fire the incision device 20. Once the trigger arm 32 reaches the firing position, the spring element 60 is displaced from the catch 66 in the housing and strikes the blade holder 40, and pushing it through the arcuate cutting cycle and into the safety position again within the housing. As will be appreciated, having the trigger arm and the opening for the lancet blade oriented on adjoining, as opposed to opposing, sides of the housing also makes the device of the present invention much easier to use.

According to the foregoing, an incision device is provided which has a very stable construction which helps prevent inadvertent firing or discharge of the device as well as enables the device to perform reliably after having been stored for a prolonged period of time, even at high temperatures. Moreover, the device has a simple construction which enables it to be manufactured and assembled in a cost-effective manner. In addition, the inadvertent depression of the trigger arm is prevented, so as to prevent wasting the incision device by accidentally firing it.

While the present invention has been described with reference to the preferred embodiments, it will be obvious to those of ordinary skill in the art that variations of the preferred embodiments may be used and that it is intended that the invention may be practiced otherwise than as specifically described herein. Accordingly, the present invention includes all modifications encompassed within the spirit and the scope of the invention as defined by the accompanying claims.

INDUSTRIAL APPLICABILITY

The present invention provides the incision device which prevents its waste caused by the inadvertent operation of a user, thus leading to more effective blood collection.

The invention claimed is:

1. An incision device for forming an incision, the incision device comprising:
   (1) a housing including a first opening;
   (2) a lancet guide assembly including a lancet body and a lancet guide, the lancet body being mounted within the housing for pivotal movement and comprising a lancet blade covered by a removable protective cover, and the lancet guide being provided for guiding the lancet blade through an arcuate cutting stroke;
   (3) a trigger mechanism including a trigger arm mounted in the housing for pivotal movement between a ready-to-fire position and a firing position, the trigger arm having a trigger actuating element; and
   (4) a spring element arranged within the housing so as to be in an unbiased condition when the trigger arm is in the ready-to-fire position and so as to be biased by engaging a catch arranged in the housing as the trigger arm pivots towards the firing position,
   wherein the housing and lancet guide assembly are configured such that during the cutting stroke, the lancet blade extends through the first opening in the housing when the lancet body is pivoted between an unfired position and a fired position;
   wherein the trigger mechanism and the spring element are configured such that the spring element in the biased condition is released from the catch arranged in the housing when the trigger arm reaches the firing position;
   wherein the spring element is arranged such that when released from the catch the spring element exerts a force on the lancet body which pivots the lancet body from the unfired position to the fired position and thereby moves the lancet blade through the cutting stroke; and
   wherein the removable protective cover comprises a stopper which prevents the trigger arm from moving to reach the firing position when the protective cover covers the lancet blade by directly contacting the trigger actuating element.

2. The incision device according to claim 1 wherein each of the trigger mechanism and the lancet body are arranged independently in the housing.

3. The incision device according to claim 1 wherein each of the lancet body and the trigger arm pivots respectively.

4. The incision device according to claim 3 wherein the lancet body pivots about a first pivot axis at an end of the lancet body and a first bearing portion arranged in the housing which corresponds to the first pivot axis, and
wherein the trigger arm pivots about a second pivot axis at an end of the trigger arm and a second bearing portion arranged in the housing which corresponds to the second pivot axis.

5. The incision device according to claim 1 wherein the trigger mechanism and the lancet body are integrally formed by a connecting portion located between them, and a notch is provided between the trigger mechanism and the connecting portion and a notch is provided between the connecting portion and the lancet body, the notches being configured to substantially allow pivot movements of the trigger mechanism and the lancet body.

6. The incision device according to claim 1 wherein the spring element is connected to the trigger arm.

7. The incision device according to claim 1 wherein the spring element has a resiliently compressible generally V-shaped configuration, an end of the spring element being connected to the trigger actuating element of the trigger arm and a free end of the spring element being engaged with the catch when the trigger arm is in the ready-to-fire position such that movement of the trigger arm from the ready-to-fire position to the firing position compresses the spring element.

8. The incision device according to claim 7 wherein the spring element is configured such that the free end of the spring element strikes and then comes over the lancet body when the biased spring element is released.

9. The incision device according to claim 1 wherein the trigger arm is configured such that when the trigger arm reaches the firing position, the trigger arm abuts against the spring element and releases the spring element from the catch.

10. The incision device according to claim 9 wherein the spring element includes a cam surface, and the trigger arm includes a cam surface which complementarily engages the cam surface of the spring element so as to release the spring element from the catch when the trigger arm reaches the firing position.

11. The incision device according to claim 1 wherein the housing includes a guide groove, and
wherein the lancet guide comprises a projecting lug carried by the lancet body which complementarily engages the guide groove.

12. The incision device according to claim 1 wherein the lancet guide assembly is configured such that the lancet blade is arranged entirely within the housing when the lancet body is in the unfired position and when the lancet body is in the fired position.

13. The incision device according to claim 1 wherein the lancet blade is carried on the lancet guide assembly by a blade holder included on the lancet body.

14. The incision device according to claim 1 wherein the trigger arm is configured such that it cannot return to the ready-to-fire position after it has been pivoted to the firing position.

15. The incision device according to claim 1 wherein the removable protective cover of the lancet guide assembly is a snap-off or pull-off removable protective cover.

16. The incision device according to claim 1 wherein the removable protective cover includes a flange portion which covers a skin-engaging portion of the housing, and
wherein the stopper is a protrusion which extends into the housing from the flange portion.

17. The incision device according to claim 1 wherein the lancet body includes an expandable section which permits linear expansion of the lancet body when the lancet body is pivoted between the unfired position and the fired position.

18. The incision device according to claim 17 wherein the expandable section has a bilaterally symmetrical shape.

19. The incision device according to claim 18 wherein the expandable section has an oval-shape.

20. The incision device according to claim 1, wherein said housing further includes a second opening,
wherein the stopper of the removable protective cover extends through the second opening when the lancet blade is covered by the removable protective cover, and
wherein the first opening is spaced apart from the second opening.

21. The incision device according to claim 1, wherein the trigger mechanism is configured such that the trigger actuating element contacts the spring element when the trigger arm is pivoted to the firing position so as to release the spring arm from the catch, and
wherein the removable protective cover is configured such that the stopper blocks a pivoting path of the trigger arm such that the trigger actuating element directly contacts the stopper and is prevented from reaching the spring element when the removable protective cover covers the lancet blade.

22. The incision device according to claim 1, wherein the housing includes an edge portion, and wherein the trigger arm includes a ridge which engages the edge portion when the trigger arm reaches the firing position so as to prevent the trigger arm from returning to the ready-to-fire position.

23. An incision device for forming an incision, the incision device comprising:
(1) a housing including a first opening;
(2) a lancet guide assembly including a lancet body and a lancet guide, the lancet body being mounted within the housing for pivotal movement and comprising a lancet blade covered by a removable protective cover, and the lancet guide being provided for guiding the lancet blade through an arcuate cutting stroke;
(3) a trigger mechanism including a trigger arm mounted in the housing for pivotal movement between a ready-to-fire position and a firing position; and
(4) a spring element arranged within the housing so as to be in an unbiased condition when the trigger arm is in the ready-to-fire position and so as to be biased by engaging a catch arranged in the housing as the trigger arm pivots towards the firing position,
wherein the housing and lancet guide assembly are configured such that during the cutting stroke, the lancet blade extends through the first opening in the housing when the lancet body is pivoted between an unfired position and a fired position;

wherein the trigger mechanism and the spring element are configured such that the spring element in the biased condition is released from the catch arranged in the housing when the trigger arm reaches the firing position;

wherein the spring element is arranged such that when released from the catch the spring element exerts a force on the lancet body which pivots the lancet body from the unfired position to the fired position and thereby moves the lancet blade through the cutting stroke;

wherein the removable protective cover comprises a stopper which prevents the trigger arm from moving to reach the firing position when the protective cover covers the lancet blade; and wherein the housing includes an edge portion, and wherein the trigger arm includes a ridge which engages the edge portion when the trigger arm reaches the firing position so as to prevent the trigger arm from returning to the ready-to-fire position.

* * * * *